United States Patent [19]

Jones

[11] Patent Number: 5,227,524
[45] Date of Patent: Jul. 13, 1993

[54] PROCESS FOR PURIFYING ACETIC ACID AND/OR ACETIC ANHYDRIDE

[75] Inventor: Michael D. Jones, Hanworth, England

[73] Assignee: The British Petroleum Company, p.l.c., London, England

[21] Appl. No.: 780,812

[22] Filed: Oct. 22, 1991

[30] Foreign Application Priority Data

Oct. 31, 1990 [GB] United Kingdom ............... 9023634

[51] Int. Cl.$^5$ ............................................. C07C 51/42
[52] U.S. Cl. ............................................. 562/608
[58] Field of Search ................................. 562/608

[56] References Cited

U.S. PATENT DOCUMENTS 4,615,806 10/1986 Hilton ............................... 562/608

Primary Examiner—José G. Dees
Assistant Examiner—Joseph M. Conrad, III
Attorney, Agent, or Firm—Brooks Haidt Haffner & Delahunty

[57] ABSTRACT

A process for removing iodide derivatives from liquid acetic acid and/or acetic anhydride comprises contacting the liquid acetic acid and/or acetic anhydride with a strong acid cation exchange resin having from about 4% to about 12% crosslinking, a surface area in the proton exchanged form of less than $10m^2g^{-1}$ after drying from the water wet state and a surface area of greater than $10m^2g^{-1}$ after drying from a wet state in which water has been replaced by methanol. The resin has at least one percent of its active sites converted to the silver form preferably from 30 to 70 percent.

9 Claims, No Drawings

PROCESS FOR PURIFYING ACETIC ACID AND/OR ACETIC ANHYDRIDE

The present invention relates to a process for removing iodide derivatives, e.g. alkyl iodides and the like, from acetic acid and/or acetic anhydride. In particular the present invention is suited to purifying acetic acid and/or acetic anhydride prepared by the rhodium catalysed, methyl iodide promoted carbonylation of methanol and/or methyl acetate.

It is known that a problem associated with acetic acid and/or acetic anhydride produced by carbonylation of methanol and/or methyl acetate in the presence of a rhodium/methyl iodide catalyst system is that, even after distillation, the acetic acid and/or acetic anhydride frequently contains small amounts of iodide impurities. Whilst the exact nature of these compounds is not known for certain, they probably comprise a mixture of methyl iodide and other higher alkyl iodides e.g. hexyl iodide. Such impurities are particularly troublesome since they poison many of the catalysts which are employed in subsequent chemical conversions of the acetic acid and/or acetic anhydride. A case in point is the catalysts used to prepare vinyl acetate from ethylene and acetic acid which are extremely sensitive to such impurities.

Several methods of removing iodine and its compounds from acetic acid and/or acetic anhydride are known. GB 2112394A, for example, teaches the use of anion exchange resins, whilst U.S. Pat. No. 4,615,806 and EP 296854 disclose the removal of iodide impurities from non-aqueous organic media such as acetic acid by the use of a silver or mercury containing macroreticular strong acid cation exchange resin such as Amberlyst 15 (Amberlyst is a Registered Trade Mark).

A problem, however, arises when the silver loaded macroreticular resins described in U.S. Pat. No. 4,615,806 and EP 296584 are used over a long period of time. This problem is particularly significant when preparing products with very low levels of iodide (e.g. less than 20 parts per billion (ppb)) from feeds containing up to 10 parts per million (ppm). In such cases it is found that, whilst silver loaded macroreticular resins are initially very effective, their efficiency declines significantly over a relatively short time. In practice this decline in efficiency is usually such as to render the resin unusable long before all the silver on it has been utilised.

It has now been found that this problem can be overcome by the use of certain ion-exchange resins intermediate in character between macroreticular resins on the one hand and gel resins on the other. Such resins, hereafter termed mesoporous resins, are characterised by a relatively low degree of crosslinking and by the fact that, whilst they have nearly gel structures when dried from a polar solvent such as water, their pore structure can be preserved if prior to drying the water is replaced by a solvent of lower polarity such as methanol.

According to the present invention there is provided a process for removing iodide derivatives from liquid acetic acid and/or acetic anhydride which comprises contacting the liquid acetic acid or acetic anhydride with a strong acid cation exchange resin having from about 4% to about 12% crosslinking, a surface area in the proton exchanged forms of less than $10m^2g^{-1}$ after drying from the water wet state and a surface area of greater than $10m^2g^{-1}$ after drying from a wet state in which water has been replaced by methanol, said resin having at least one percent of its active sites converted to the silver form.

The process of the present invention is particularly suited to reducing the levels of iodide derivatives, e.g. $C_1$ to $C_{10}$ alkyl iodides, in the acetic acid or acetic anhydride from levels of up to 10 ppm down to levels of less than 10 ppb, most preferably to reducing the iodide content from about 500 ppb to less than 5 ppb.

Mesoporous resins are defined as styrene/divinyl benzene copolymers having from about 4 to about 12% preferably from 6 to 10% crosslinking. Such resins are further characterised in that when dried from the water wet state in the proton exchanged form they have a surface area of less than $10m^2g^{-1}$ preferably less than $8m^2g^{-1}$ whilst when dried from a wet state in which water has been replaced by methanol, they have a surface area greater than $10m^2g^{-1}$ preferably greater than $15m^2g^{-1}$. The surface areas given above are those measured by the nitrogen BET method and the methods used to effect drying are those referred to as METHODS A and B below.

Particularily preferred examples of mesoporous resins are those materials which are sold under the trade names Purolite C145, Purolite CT145, Bayer K2441 and Bayer K2411.

The amount of silver present on the resin to be used is suitably such that at least one percent of the active sites which can be occupied by metal cations are loaded, preferably 10 to 90 percent of the sites, most preferably 30 to 70 percent. The silver-loaded resins can be prepared by ion-exchange or impregnation techniques, known in the art. A preferred method is that described in EP 296584 involving slurrying a sample of the resin in the proton exchanged form with silver oxide in water and thereafter treating the slurry with a carboxylic acid preferably acetic acid.

The process of the present invention is suitably carried out by passing liquid acetic acid or acetic anhydride contaminated with the iodide derivatives through a fixed bed of the resin at a predetermined rate. Preferably the resin bed is graded by backflushing before use. The feed rate used will depend on a number of variables including the amount of iodide impurities in the acetic acid or acetic anhydride, the degree of acid or anhydride purity required and the particular resin employed. Typical flow rates are in the range 0.5 to 50 bed volumes per hour, preferably 5 to 15. Optimum flow rates will depend upon temperature and can be readily determined.

The temperature at which the process is carried out must be high enough to prevent acetic acid or acetic anhydride from freezing at one extreme or boiling at the other. Typical ranges are 20° to 120° C. preferably 25° to 100° C. Whilst in general it is desirable to operate at as high a temperature as possible, in order to effect maximum removal, it may, in certain circumstances for reasons of economy, be desirable to operate at a lower temperature and modify one of the other process variables to reach the target level of iodide removal. The stability of the resins may also impose an upper limit on the operating temperature.

The process of the present invention will now be illustrated by the following Examples.

EXAMPLE 1

Purolite C145 (Mesoporous Resin)

112.5 g (143 ml) of the wet resin (as supplied) was charged to a 500 ml pot equipped with a 5 cm diameter PTFE impeller. Distilled water (100 ml) was added and the mixture stirred at 60 rpm for 15 minutes. The water was then drawn off and another 100 ml of distilled water added. This procedure was then repeated (total washings 3×100 ml water). Silver (1) oxide (9.5 g-ex Aldrich) was added together with enough distilled water to cover the solids (ca 100 ml). The mixture was stirred at 60 rpm for 1 h at room temperature to thoroughly mix the reactants. Acetic acid (75 ml) was then added and the mixture heated to 50° C. for 3 h whilst being stirred at 60 rpm. The resin was filtered off, washed with acetic acid (2×150 ml) and dried under flowing air.

EXAMPLE 2

Bayer K2411 (Mesoporous Resin)

The method above was repeated using Bayer K2411 resin 125.0 g (174 ml) and silver oxide (9.5 g).

COMPARATIVE TEST A

Amberlyst 15 (Macroreticular Resin)

The method above was repeated using Amberlyst 15 resin 87.0 g (100 ml) and silver oxide (7.7 g).

COMPARATIVE TEST B

Amberlite IR120 (Gel Resin)

The method above was repeated using Amberlite IR120 resin 70 g (82 ml) and silver oxide (6.9 g).

The products of Examples 1 and 2 and Comparative Tests A and B were analysed for silver. The results are shown in Table 1 below.

TABLE 1

| Resin | *Ag (% w/w) | H+ Exchange Capacity (mol/L$_{resin}$) | % of Site Silver Exchanged |
|---|---|---|---|
| Purolite C145 | 12.5 | 1.6 | 35.8 |
| Bayer K2411 | 10.2 | 1.25 | 37.7 |
| Amberlyst 15 | 11.8 | 1.8 | 33.5 |
| Amberlite IR120 | 10.5 | 1.95 | 37.2 |

*Resins predried in oven at 100° C. for ½ hr prior to analysis.

Surface Area Measurements on Dry Resins a. Methods for Drying the Resin

METHOD A—Drying of Resin from Water Wet State

A 100 ml sample of the water wet resin as supplied was heated at 105° C. to achieve a final pressure of ca 0.5 mbar of mercury after 4 hours.

METHOD B—Drying of Resin from Methanol Wet State

A 100 ml sample of the water wet resin was washed on a coarse sinter with seven volumes of methanol (approx 5–10 minutes). Thereafter the methanol wet resin was heated to 50° C. at a pressure of 20 mm of mercury for 30 minutes and then at 105° C. to achieve a final pressure of ca 0.5 mbar of mercury after 4 hours.

b. Surface Area Measurements

Methods A and B were applied to samples of the resins Purolite C145 (mesoporous) and Amberlyst 15 (macroreticular), Bayer K2411 (mesoporous) and Amberlite IR 120 (Gel).

The products of these experiments were then subjected to $N_2$ BET to measure their surface areas.

TABLE 2

| Resin | Type | Surface Area by $N_2$ BET ($m^2/g$) Drying Method A | Drying Method B |
|---|---|---|---|
| Purolite C145 | Mesoporous | 7 ± 1 | 20 ± 1 |
| Amberlyst 15 | Mescroreticular | 41 ± 1 | 44 ± 1 |
| Bayer K2411 | Mesoporous | <5 | 20 ± 1 |
| Amberlite IR120 | Gel | <5 | <5 |

General Procedure for Purifying Acetic Acid 25 mls of the silver loaded resin was charged to a column (1 cm diameter) containing acetic acid. The resin bed was then backflushed to remove any fines and to classify the resin particles according to size. Acetic acid dosed with 60 ppm iodide (added as hexyl iodide) was pre-heated to 43° C. and passed downflow through the resin bed heated to 43° C. The resin bed was fitted with a weir system to ensure that it operated liquid full. Samples of the treated acetic acid were collected at intervals and analysed for iodide by neutron activation analysis.

Using the procedure described above silver loaded versions of the resins were tested as follows:

Example 3—Bayer K2411 (Mesoporous)
Comparative Test C—Amberlyst 15 (Macroreticular)
Example 4—Purolite C145 (Mesoporous)
Comparative Test D—Amberlite IR120 (Gel).

The results given in Table 3 below show that under equivalent conditions the two mesoporous resins (Purolite C145 and Bayer K2411) are superior to both Amberlyst 15 (marcroreticular resin) and Amberlite IR120 (gel resin) in terms of lifetime.

TABLE 3

| Hours on Stream | Bayer K2411 I in Product (ppb by NAA) | % I removed | Amberlyst 15 I in product (ppb by NAA) | % I removed | Purolite C145 I in product (ppb by NAA) | % I removed | Amberlite IR120 I in product (ppb by NAA) | % I removed |
|---|---|---|---|---|---|---|---|---|
| 3 | | | | | | | 59000 | — |
| 11 | | | 13.6 | 99.98 | | | | |
| 12 | | | | | | | 62000 | — |
| 13 | <18 | 99.98 | | | | | | |
| 16 | | | | | | | 60500 | — |
| 20 | | | | | <18 | 99.98 | | |
| 21 | 40 | 99.93 | | | | | | |
| 24 | | | | | | | 60000 | — |
| 27 | | | 13.9 | 99.98 | | | | |
| 31 | | | 22.0 | 99.96 | | | | |
| 32 | | | | | 37.0 | 99.94 | 60000 | — |

TABLE 3-continued

| Hours on Stream | Bayer K2411 I in Product (ppb by NAA) | Bayer K2411 % I removed | Amberlyst 15 I in product (ppb by NAA) | Amberlyst 15 % I removed | Purolite C145 I in product (ppb by NAA) | Purolite C145 % I removed | Amberlite IR120 I in product (ppb by NAA) | Amberlite IR120 % I removed |
|---|---|---|---|---|---|---|---|---|
| 33 | 31 | 99.95 | | | | | | |
| 40 | | | | | <18 | 99.98 | | |
| 41 | 52 | 99.91 | | | | | | |
| 43 | | | 81.2 | 99.86 | | | | |
| 59 | | | 601.0 | 99.00 | | | | |
| 60 | | | | | 22.0 | 99.96 | | |
| 61 | 168 | 99.72 | | | | | | |
| 67 | | | 1192.0 | 98.01 | | | | |
| 68 | | | | | 49.9 | 99.92 | | |
| 69 | 232 | 99.61 | | | | | | |
| 77 | 516 | 99.14 | | | | | | |
| 79 | | | 3273.0 | 94.54 | | | | |
| 80 | | | | | 174.0 | 99.71 | | |
| 92 | | | | | 714.0 | 98.81 | | |
| 95 | | | 8770.0 | 85.36 | | | | |
| 104 | | | | | 2455.0 | 95.90 | | |
| 105 | 7140 | 88.08 | | | | | | |
| 107 | | | 14400.0 | 75.96 | | | | |
| 116 | | | | | 4526.0 | 92.44 | | |
| 119 | | | 21000.0 | 64.94 | | | | |
| 135 | | | 33500.0 | 44.07 | | | | |

I claim:

1. A process for removing iodide derivatives from liquid acetic acid and/or acetic anhydride which comprises contacting the liquid acetic acid or acetic anhydride feedstock with a strong acid mesoporous cation exchange resin having from about 4% to about 12% crosslinking, a surface area in the proton exchanged form of less than 10 $m^2g^{-1}$ after drying from the water wet state and a surface area of greater than 10 $m^2g^{-1}$ after drying from a wet state in which water has been replaced by methanol, said resin having at least one percent of its active sites converted to the silver form.

2. A process as claimed in claim 1 wherein the strong acid cation exchange resin has from 6 to 10% crosslinking.

3. A process as claimed in claim 1 or claim 2 wherein the strong acid cation exchange resin has a surface area of less than 8 $m^2g^{-1}$ after drying from the water wet state and a surface area of greater than 15 $m^2g^{-1}$ after drying from a wet state in which water has been replaced by methanol.

4. A process as claimed in claim 1 wherein from 10 to 90 percent of the active sites of the strong acid cation exchange resin are converted to the silver form.

5. A process as claimed in claim 4 wherein from 30 to 70 percent of the active sites of the strong acid cation exchange resin are converted to the silver form.

6. A process as claimed in claim 1 wherein the liquid acetic acid and/or acetic anhydride used as feedstock contains up to about 500 parts per billion of the iodide derivatives.

7. A process as claimed in claim 1 wherein contact between the acetic acid and/or acetic anhydride and the strong acid cation exchange resin is achieved by passing the acetic acid and/or acetic anhydride through a fixed bed of the strong acid cation exchange resin.

8. A process as claimed in claim 7 wherein the fixed bed of the strong acid cation exchange resin is graded by backflushing before use.

9. A process as claimed in either claim 7 or claim 8 wherein the flow rate of acetic acid and/or acetic anhydride through the fixed bed is in the range 5 to 15 bed volumes per hour.

* * * * *

UNITED STATES PATENT AND TRADEMARK OFFICE
CERTIFICATE OF CORRECTION

PATENT NO. : 5,227,524
DATED : July 13, 1993
INVENTOR(S) : MICHAEL D. JONES

It is certified that error appears in the above-indentified patent and that said Letters Patent is hereby corrected as shown below:

Col. 4, l. 26, Table 2, correct the spelling of the word "Macroticular"

Signed and Sealed this

Twenty-fourth Day of May, 1994

Attest:

BRUCE LEHMAN

Attesting Officer     Commissioner of Patents and Trademarks